(12) United States Patent
Woolfson et al.

(10) Patent No.: US 10,470,584 B2
(45) Date of Patent: Nov. 12, 2019

(54) SYSTEM, APPARATUS AND METHOD FOR MEASURING BODY CHARACTERISTICS

(71) Applicant: CHAPELGLADE LIMITED, Dublin (IE)

(72) Inventors: David Woolfson, County Dublin (IE); Duncan Bain, Hertfordshire (GB)

(73) Assignee: Chapelglade Limited, Dublin (IE)

( * ) Notice: Subject to any disclaimer, the term of this patent is extended or adjusted under 35 U.S.C. 154(b) by 329 days.

(21) Appl. No.: 15/113,012

(22) PCT Filed: Jan. 26, 2015

(86) PCT No.: PCT/EP2015/051513
§ 371 (c)(1),
(2) Date: Jul. 20, 2016

(87) PCT Pub. No.: WO2015/110639
PCT Pub. Date: Jul. 30, 2015

(65) Prior Publication Data
US 2017/0020301 A1    Jan. 26, 2017

(30) Foreign Application Priority Data

Jan. 24, 2014 (GB) .................................. 1401227.2

(51) Int. Cl.
*G06G 7/48* (2006.01)
*A47C 31/12* (2006.01)
*A61B 5/00* (2006.01)
*A61B 5/107* (2006.01)
*G06F 17/50* (2006.01)

(52) U.S. Cl.
CPC .......... *A47C 31/123* (2013.01); *A61B 5/0064* (2013.01); *A61B 5/1077* (2013.01);
(Continued)

(58) Field of Classification Search
None
See application file for complete search history.

(56) References Cited

U.S. PATENT DOCUMENTS 5,148,706 A * 9/1992 Masuda ............... A47C 31/123
5/1
9,033,901 B2 5/2015 Woolfson
(Continued)

FOREIGN PATENT DOCUMENTS

DE    102004001182 A1 * 7/2005 ........... A47C 31/123
JP    2007-151817         6/2007
JP    2007151817 A  * 6/2007 ........... A47C 31/123

OTHER PUBLICATIONS

Bain, Duncan "Development of a Phantom for the Assessment of Patient Support Systems for the Prevention of Pressure Sores", 1997, Department of Physics, University of Surrey. (Year: 1997).*
(Continued)

*Primary Examiner* — Cedric Johnson
(74) *Attorney, Agent, or Firm* — Faegre Baker Daniels LLP

(57) ABSTRACT

The invention provides a system for using optical mapping for producing a 3 dimensional mapping of the characteristics of a body; the system comprising measuring the movement of at least one registration mark on a capture sheet along a predetermined axis and means for using this measurement of the movement of the at least one registration mark to provide an indicator of the characteristics of the body. The invention also provides an apparatus for measuring body characteristics and a method of measuring body characteristics.

14 Claims, 10 Drawing Sheets

(52) U.S. Cl.
CPC .......... *A61B 5/1079* (2013.01); *A61B 5/6892* (2013.01); *A61B 5/702* (2013.01); *G06F 17/50* (2013.01); *A61B 5/447* (2013.01)

(56) References Cited

U.S. PATENT DOCUMENTS

| 9,848,712 | B2* | 12/2017 | Main ...................... A47C 31/12 |
| 2006/0239538 | A1* | 10/2006 | Sato ..................... A61B 5/0064 |
| | | | 382/154 |
| 2013/0002832 | A1 | 1/2013 | Lasenby et al. |
| 2013/0035599 | A1 | 2/2013 | De Bruijn et al. |
| 2013/0144751 | A1 | 6/2013 | Gorjanc et al. |

OTHER PUBLICATIONS

International Search Report dated May 29, 2015 in International Application No. PCT/EP2015/051513.

Bain D, Laboratory performance of alternating pressure air mattresses component and sequelae. Br J Nurs. Nov. 2011, vol. 20 No. 20, 6 pages.

Bain D, Ferguson-Pell M, McLeod A Evaluation of mattresses using interface pressure mapping. J Wound Care. Jun. 2003, vol. 12 No. 6, 5 pages.

Bain D, Scales J T, Nicholson G P A new method of assessing the mechanical properties of patient support systems (PSS) using a phantom. A preliminary communication. Med Eng Phys. Jun. 1999, vol. 21 No. 5, 9 pages.

Bain D, Testing the Effectiveness of Patient Support Systems: The Importance of Indentor Geometry, Journal of Tissue Viability, Jan. 1998; vol. 8 No. 1, 3 pages.

Jacobson B H, Gemmell, Hayes, Altena, Effectiveness of a Selected Bedding System on Quality of Sleep, Low Back Pain, Shoulder Pain, and Spine Stiffness. JMPT, Feb. 2002; vol. 25 No. 2, 5 pages.

Bain D., "Development of a phantom for the assessment of patient support systems for the prevention of pressure sores," PhD Thesis, 1997, 211 pages.

* cited by examiner

SYSTEM, APPARATUS AND METHOD FOR MEASURING BODY CHARACTERISTICS

CROSS-REFERENCE TO RELATED APPLICATIONS

This U.S. patent application is a National Stage entry under 35 U.S.C. 371 of International Application No. PCT/EP2015/051513, filed on Jan. 26, 2015.

FIELD OF THE INVENTION

The present invention relates to a system and method for measuring body characteristics. The system and method of the present invention are relevant, in particular, but not solely, for mattress selection according to a particular person's body characteristics.

BACKGROUND OF THE INVENTION

When buying or choosing a mattress, there is currently little information to guide the user, in terms of selecting a mattress that will suit his/her particular body characteristics. Mattresses are presented as a general range from basic quality to high quality, with no account taken of the particular physique of the user, and no attempt to match mattress characteristics to the physical characteristics of the user. This contrasts sharply with, for example, the selection process for shoes where the selection process involves taking into account the physical characteristics of the user including foot length, width, and arch height are taken into account when selecting the shoe, and shoes are categorised according to the relevant parameters.

Recent research (Bain 1997 Phd Thesis, University of Surrey) has indicated that certain relationships exist between user physique and optimal mattress characteristics. For example, to maintain spinal alignment when lying on the side (generally recognised as desirable to prevent back pain) the optimal firmness of the mattress depends on the breadth from the saggital plane of bony prominences such as the greater trochanter and ilium, and on the body mass distribution of the user. The mattress needs to provide the correct amount of resistance to allow these bony prominences to displace into the mattress the correct distance to preserve a straight spine. The amount of resistance required depends on the user parameters mentioned.

When lying on the back, it is generally recognised that the natural curvature of the spine, including a lumbar curve, a thoracis curve, and a cervical curve, should be maintained for comfort. Once again, it has been shown that the optimal characteristics of the mattress to maintain these curves depends on the individual user shape. For example, a user with a tighter (smaller radius) lumbar curve may require a mattress with greater differential yield between adjacent regions of the mattress. This has implications, not only for the firmness of the mattress, but also in the spatial resolution (e.g. springs per square meter, or foam profile density) of the support, and the tensile properties of the top layers of padding. A mattress that is soft overall, but has a very coarse distribution of springs, or a stiff, hammock-like cover, will not be able to accommodate a tightly accentuated lumbar curve.

Some steps have been taken previously in an attempt to provide information relating to the individual user that may be used to inform the choice of mattress.

One example is pressure mapping. In this method, a pressure mapping device, consisting of a two-dimensional array of pressure sensors, is used to display a two-dimensional map of the pressure distribution on the skin of the user when lying on the mattress. Nominally, certain parameters in the mattress may be modified to optimise the pressure distribution. This method has a number of problems. One problem is that it is not well understood what would constitute a good or bad pressure distribution, in terms of maintaining a good posture. Current understanding and interpretation of pressure maps is focused predominantly on the issue of pressure ulcers in hospital patients and so is more concerned with locating areas of high pressure which may lead to poor skin perfusion. Strategies for adjusting inflation pressures to minimise peak pressure values may be effective in maintaining skin health but will be of little value for maintaining good sleeping posture.

Furthermore, pressure mapping technologies are expensive, and the expense may be prohibitive in many retail establishments. A great deal of specialist scientific expertise is also required to maintain, calibrate, and operate pressure mapping systems in such a way as to obtain valid results. This level of expertise is very unlikely to be on hand in a retail context.

More recently (Bain, Hubbard, Woolfson) a system was developed for capturing a basic, simplified shape of the body. This shape could then be used alongside historical data relating body shape to mattress preferences. This system is published in United States patent specification no. US 2011/0009776.

However, this system also exhibited certain limitations. The 3 dimensional shape of the body was not captured. Information about the body type was only inferred from 2-dimensional silhouettes in front view and side view, and therefore relied on some broad assumptions, and could only broadly categorise body types.

Furthermore, the capture of the body shape in the standing position was considered by some skilled in this area, to be unrepresentative of the body shape while lying down, although it was also widely acknowledged that the shape captured while lying down would represent a non-ideal condition, with the body posture already distorted.

SUMMARY OF THE INVENTION

The present invention relates to an inexpensive system and apparatus, requiring little precision in set-up or operation, for measuring and analysing the salient parameters of the individual user, for the purposes of assisting with mattress selection. The present invention provides a system for using optical mapping for producing a 3 dimensional mapping of the characteristics of a body; the system comprising means for measuring the movement of at least one point on the body along a predetermined axis and means for using this measurement of the movement of the at least one point to provide an indicator of the characteristics of the body.

It is to be understood that references to "person" and "body characteristics" throughout this specification are to be construed to mean a human or animal and a human or animal body, respectively. Thus, the present invention is applicable to both human and animal bedding.

Preferably, the system comprises apparatus having a flexible surface configured for capturing the extent of movement of the flexible surface when a body is placed on the flexible surface.

Ideally, the system comprises apparatus having a flexible surface configured for measuring the extent of movement of the flexible surface when said body is placed on said flexible surface and means for providing an effective pressure to be exerted on the body that is less than the pressure exerted by gravity.

They system preferably comprises a supporting means and a flexible surface and wherein the flexible surface and the supporting means cooperate together to allow the interface between a body placed on or against the flexible surface to be modelled.

The supporting means may optionally comprises a support frame, support biased means such as springs, or a platform, preferably a rigid platform.

The system may comprise means for combining the 3-dimensional shape and/or pressure distribution information with existing data relating these parameters to mattress preference in order to provide a recommendation for mattress selection.

In a further aspect, the present invention provides an apparatus for measuring body characteristics relevant, in particular, for mattress selection, the apparatus comprising a capture sheet configured to allow the interface between a body and a support surface to be modelled, preferably modelled with reduced pressure between the body and the support surface. The apparatus may comprise means for combining the 3-dimensional shape and/or pressure distribution information with existing data relating these parameters to mattress preference, in order to provide a recommendation for mattress selection.

Advantageously, in this embodiment, the interface is characterised by measuring the shape of the subject while recumbent on the inclined platform.

Conveniently, the interface is characterised by measuring the interface pressure distribution between the subject and the interface, preferably, wherein measuring the interface pressure distribution is achieved by causing a sheet material to drape over the shape of the subject, and the shape of this material is then recorded.

Preferably, recordal of the shape of the material is carried out by obliquely photographing registration points on marked or projected on the sheet material.

Alternatively, recordal of the shape of the material is carried out by stereoscopically photographing registration points marked or projected on the sheet.

Preferably, the registration points are projected from one angle, and photographed from another angle, to yield 3-dimensional positional information.

Most preferably, the registration points on the sheet will move approximately perpendicular to the platform plane, allowing an approximation of 3-dimensional shape using only one camera.

In a still further aspect, the present invention also provides a method of using optical mapping for producing a 3-dimensional mapping of the characteristics of a body. Thus, the present invention provides a method that includes combining the 3-dimensional shape and/or pressure distribution information with existing data relating these parameters to mattress preference in order to provide a recommendation for mattress selection.

Technology exists for determining the mechanical properties of mattresses including indentation hardness, ability to conform to detailed shape, and the speed of viscous recovery to deflection. Previous work has demonstrated that persons with various different body types are supported best on mattresses having respective associated different properties. For example, a very lightweight person with sharp bony protuberances will require a very soft surface, so that the bony shapes will be accommodated with little force, thus distributing pressure over a large area. A large, heavy person, however, will sink right through such a mattress, and rest on the hard surface beneath. As a further example, a heavy person on a mattress comprising the slow-moving visco type of foam will tend to get stuck in a "dent", formed over many minutes of lying, so that subsequent turning or repositioning becomes difficult. A lighter, more agile person will not experience such problem but will benefit from the improved conforming properties of the visco foam. Further physical properties such as shoulder width, hip width, apple- or pear-type obesity, natural spinal curvature in the lumbar, thoracis, and cervical regions, all have implications for the preferred mattress type, which have been validated empirically by individual consumer preferences, and related to individual consumer shapes.

The system, apparatus and method of the present invention operates in any of the embodiments described herein, be it with the capture sheet connected to a horizontal rigid platform, for the purposes of direct capture of recumbent position, or from a vertical rigid platform, for a direct capture of standing position, or all points in between, for varying degrees of 'reduced effective gravity' recumbent position.

In an alternative embodiment, a reduced-functionality version of the system, apparatus and method of the present invention is provided which uses a pressure mapping array instead of the flotation fabric. Pressure-mapping involves measuring the interface pressure measurement between a body and a support surface by use of a system of sensors or transducers distributed upon, in or under the surface in the form of a sensor map or otherwise. On its own, this reduced functionality embodiment, without the inclusion of a capture sheet, camera and the capacity to provide 3D image data will provide enhanced or "more accurate" pressure mapping data as the body shape distortion caused when a body interfaces with a support surface at full gravity will be obviated.

In this alternative embodiment, the system will give no 3D information about body contours, or spinal curves. However, it will provide a map of the pressure distribution on the base, which may be fitted with a thin standardised cellular foam mattress above the pressure mapping array. So, while this alternative, reduced functionality, pressure mapping embodiment of the present invention will not give all the postural information possible with the first embodiment of the system, apparatus and method of the present invention using the capture sheet 3 connected to the rigid platform 1 (i.e the "flotation fabric" embodiment with a flexible capture sheet and supporting means), the lower functionality, pressure mapping embodiment enables collection of information which can provide a valid basis for mattress recommendation.

In a still further, alternative embodiment comprises the system and apparatus which is enabled with both the pressure mapping and capture sheet with supporting means/3D imaging methods so as to capture the biometric data from different perspectives.

In a further alternative embodiment, the system may comprise means for adjusting the inflation properties of the air chamber between the flexible sheet/capture sheet and the base platform whereby the inflation properties of the air chamber between the capture sheet and the base platform may be adjusted, for example, by adjusting the inflation pressure, while examining the effects on posture in real time. For example, the 3-dimensional representation of the lumbar, thoracic, and cervical curves can be continuously monitored, while the inflation pressure (and so the firmness) of the support are adjusted. This allows the prescription of the ideal firmness properties of a mattress for the individual.

This may be performed with the system horizontal, or inclined with suitable correction factors.

Further features of the system, apparatus and method of the present invention are set forth in the appended Claims.

BRIEF DESCRIPTION OF THE DRAWINGS

The present invention will now be described with reference to the accompanying drawings in which are shown, by way of example only, one embodiment of the system and apparatus of the present invention.

In the drawings:

FIG. 2a is a side view of the apparatus shown in FIG. 1, with a person leaning against the platform, BEFORE the fabric on the platform is urged against the person's outline;

FIG. 2b is a rear view of the apparatus shown in FIG. 2a;

FIG. 3a is a side view of the apparatus shown in FIG. 2a, with a person leaning against the platform, AFTER the fabric on the platform has been urged against the person's outline;

FIG. 3b is a rear view of the apparatus shown in FIG. 3a;

FIG. 4 shows a rigid base/platform comprising a frame surround, which traps the edges of a flexible capture sheet, laid on top of the platform;

DETAILED DESCRIPTION OF THE INVENTION

Figure 1:
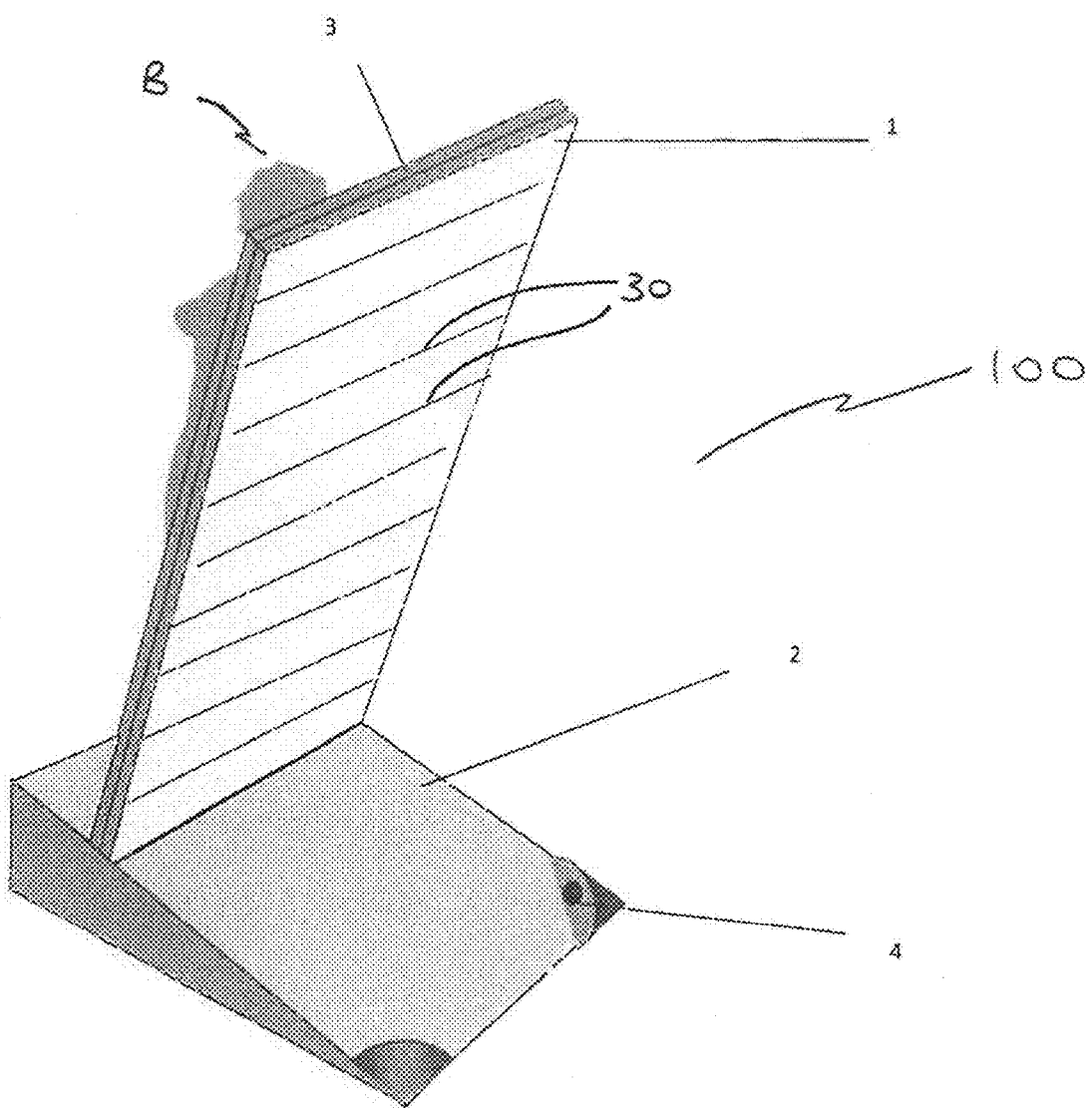
FIG. 1 is a perspective view of one embodiment of the apparatus, showing the outline of a person leaning against the support platform of the apparatus which in this embodiment is extending upwardly at an angle to the horizontal plane.

Referring initially to FIG. 1, one embodiment of the apparatus of the invention is indicated generally by reference numeral 100. The apparatus 100 comprises capture sheet 3 and a capture sheet supporting means, which in this embodiment comprises a transparent platform 1, for example, of toughened glass. In this embodiment, the platform 1 is supported by a base 2 which is inclined at an angle from the vertical plane. This angle is selected such that the person is inclined against the platform. Thus, the angle of the platform relative to the vertical plane may be, for example, 15 degrees, but may be less or more to give similar effect. However, it is to be understood that any angle of inclination of the platform, from horizontal to vertical, and all points in between, will enable the system, apparatus and method of the present invention to be operated effectively, The bottom edge of the transparent platform 1 is provided with a base 2 at right angle to the platform 1.

Thus, when the customer stands on the base, and leans back against the transparent platform 1, his/her feet are in a natural position, and the forces exerted between the body B and the capture sheet 2 are substantially reduced relative to the forces which would be exerted if the customer was lying on a horizontal platform, according to the cosine of the angle between the platform 1 and the horizontal plane.

Draped on the upper surface of the glass is a capture sheet 3 which may be in the form of a flexible fabric 3. The capture sheet 3 is selected from a fabrics that are drapable for example, a stretch Lycra fabric. The capture sheet 3 is marked with registration marks which is in the form of a printed pattern (eg a pattern of horizontal lines 30) on the side of the fabric 3 facing the transparent platform 1. The capture sheet 3 has a printed pattern 30 such as a pattern of horizontal lines 30 (shown in this particular embodiment), a grid, or other regular pattern. Alternatively, the grid or horizontal lines or other pattern or landmarks may be projected onto the rear of the capture sheet 3 using a laser, projector or other means.

The other side of the capture sheet 3 (i.e. the side of the capture sheet 3 with which the body B will be in contact when the system and method are in use) may be treated with a coating or other treatment to aid cleanability and durability.

The material from which the capture sheet 3 is formed is selected so that its properties enable it to function as a "flotation fabric". By this term is meant that the capture sheet 3 can describe the shape of the body B as if the body B was floating i.e. supported in ideal conditions from a pressure distribution perspective.

Preferable properties of capture sheet are that it drapes well to the shape of the body, and is lightweight, so as to be easily blown without causing artefact. Artefact may be caused from the weight of the capture sheet 3 causing the capture sheet 3 to sag; or from excessive air pressure or air flow required to cause the capture sheet 3 to drape over the body causing deformation of soft body tissues.

Ideally, the capture sheet 3 is formed of material that can be stretched, preferably in all directions, although this is by no means essential. Preferably, the capture sheet 3 is formed of a stretchable fabric that is relatively thin. Also preferably, the capture sheet has a coating allowing it to be less pervious to air than a flexible sheet manufactured of a material without a coating, thereby facilitating the process of ensuring the capture sheet 3 is blown onto/against the body B, as well as making it easier to print suitable registration marks (such as the horizontal lines pattern 30) on the rear of the capture sheet 3.

The capture sheet 3 may be held onto the glass by a fixing means such as a clamp. The fixing means may be in the form of a frame surround 11, which functions to clamp the edges of the capture sheet 3 to the transparent platform 1. Alternatively, the fixing means may comprise any other suitable fixing means for securing the capture sheet 3 to the transparent platform 1.

Means for urging the capture sheet 3 against the body B, such as a person's body, are provided, for instance, a high-flow blower (not shown), such as, a blower of the type used for inflating promotional inflatables, bouncy castles, or camping mattresses, is used to blow the fabric urging it against the back of the person and extending along the entire length of the person, thereby causing it to drape over the subject being measured.

An air pressure sensor (not shown) may also be included to measure the air pressure.

Positioned on at least one rear corner of the platform is at least one camera 4, configured to capture the registration marks printed on the back of the capture sheet 3; and more particularly, the at least one camera 4 is configured to capture distortions in the pattern of the registration marks caused by the body B coming into contact with the capture sheet 3.

Figure 2:
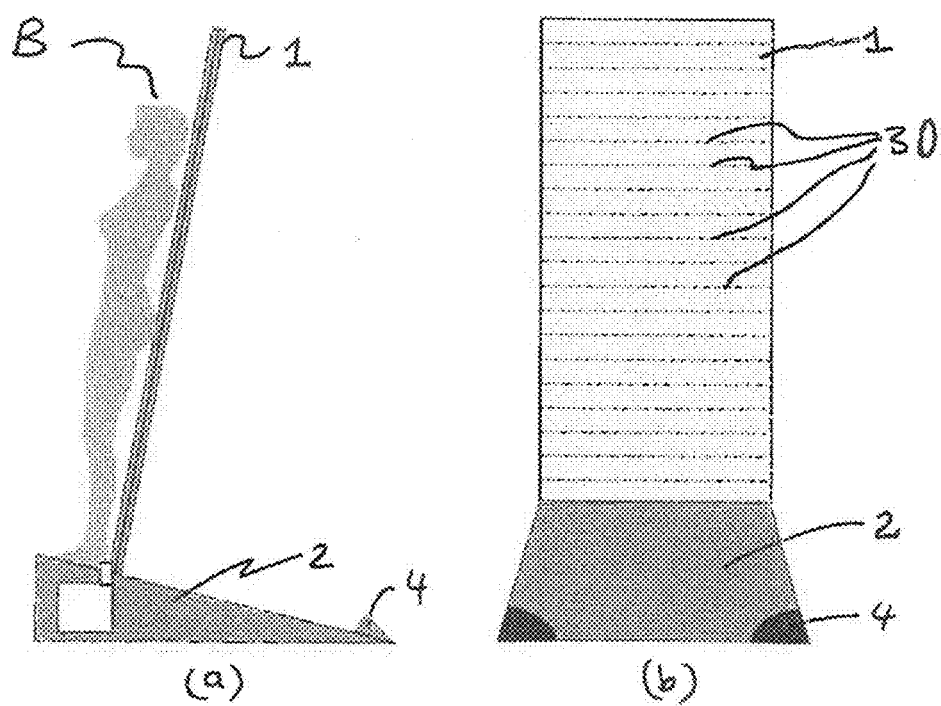

Initially, as shown in FIG. 2b, the undisturbed pattern of the capture sheet 3 is visible to the naked eye and is detected by the camera 4.

Figure 3:
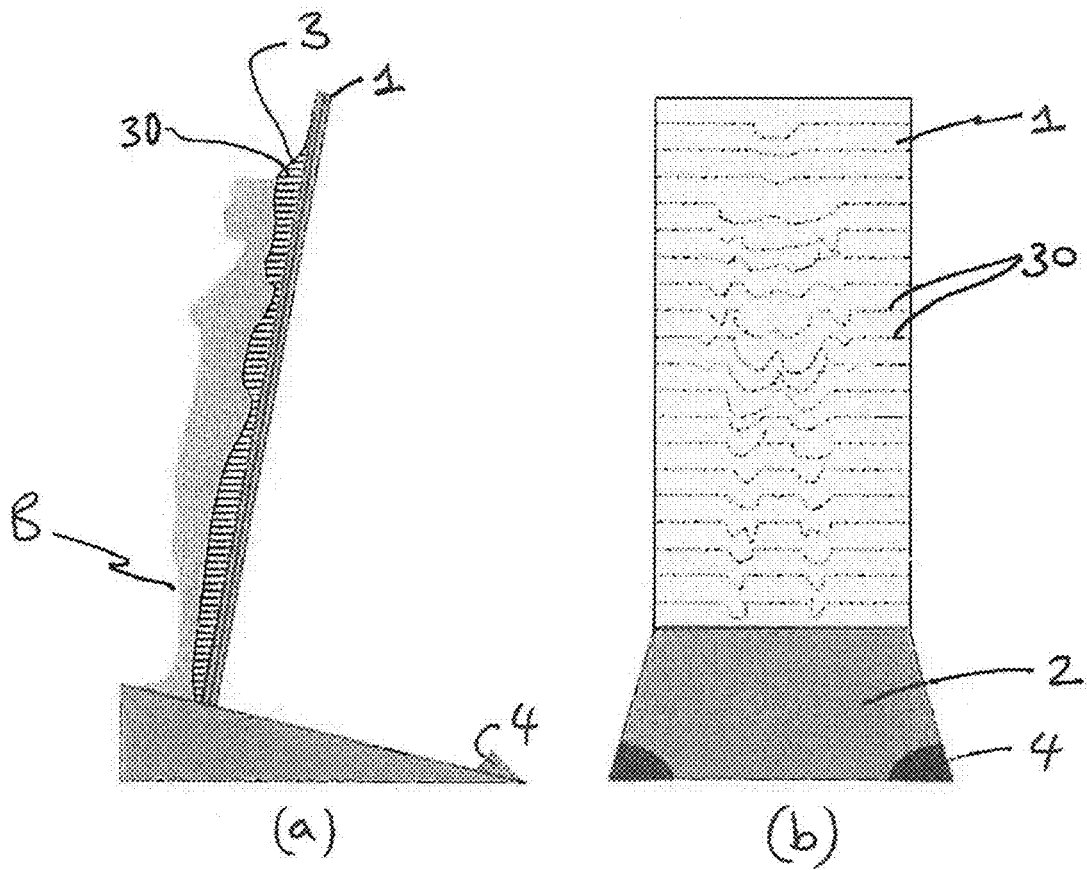

As the blower is activated and operates to supply air into the space between the sheet and the rigid platform, and the back of the fabric is pressurised, and it is urged against the back of the person leaning against the platform 1; the capture sheet 3 drapes to and along the back of the body B such as a person who is a customer wanting to purchase a custom-made mattress which will specifically be manufactured to match that person's physical requirements, according to FIG. 3.

As the capture sheet 3 drapes the body B, perturbations in the registration marks pattern 30 define the body shape in three dimensions (3D) These perturbations may be visualised either stereoscopically using two cameras, or more simply inferred with little loss of accuracy by a single camera viewing the movement of the reference points on the grid from the original plane, using simple Pythagorean triangulation, and assuming that each point has moved nearly orthogonally from the original position. This is recorded by the cameras 4, and quantified by image processing algorithms, to deliver an approximation to the 3-Dimensional shape of the body, particularly, the rear of the body B.

Over a decade of research (Bain et al; references included in Reference section later in this patent specification) has established known relationships between body morphology and mattress characteristics. See e.g. Bain D, Laboratory performance of alternating pressure air mattresses component and sequelae. Br J Nurs. 2011 Nov. 10-23; 20(20): S29-34; Bain D, Ferguson-Pell M, McLeod A Evaluation of mattresses using interface pressure mapping. J Wound Care. 2003 June; 12(6): 231-5; Bain D, Scales J T, Nicholson G P A new method of assessing the mechanical properties of patient support systems (PSS) using a phantom. A preliminary communication. Med Eng Phys. 1999 June; 21(5): 293-301; Bain D, Testing the effectiveness of patient support systems: the importance of indentor geometry. J Tissue Viability. 1998 January; 8(1): 15-7; and Jacobson B H 1, Gemmell H A, Hayes B M, Altena T S. Effectiveness of a selected bedding system on quality of sleep, low back pain, shoulder pain, and spine stiffness. J Manipulative Physiol Ther. 2002 February; 25(2): 88-92.

Measuring the body morphology at "low gravity", i.e. in the 10-15 degree tilted position, provided by the apparatus and system of the present invention, allows the capture of a realistic recumbent position, but with spinal curvatures and soft tissue topology undistorted by the pressures that would be experienced under full gravity. The apparatus, system and method of the present invention captures this realistic recumbent position at "low gravity" and this in turn, enables the optimal recumbent shape, to be preserved as far as possible by the mattress, that will be manufactured to the specific requirements of the individual body, when the body is lying in the horizontal position.

Figure 4:
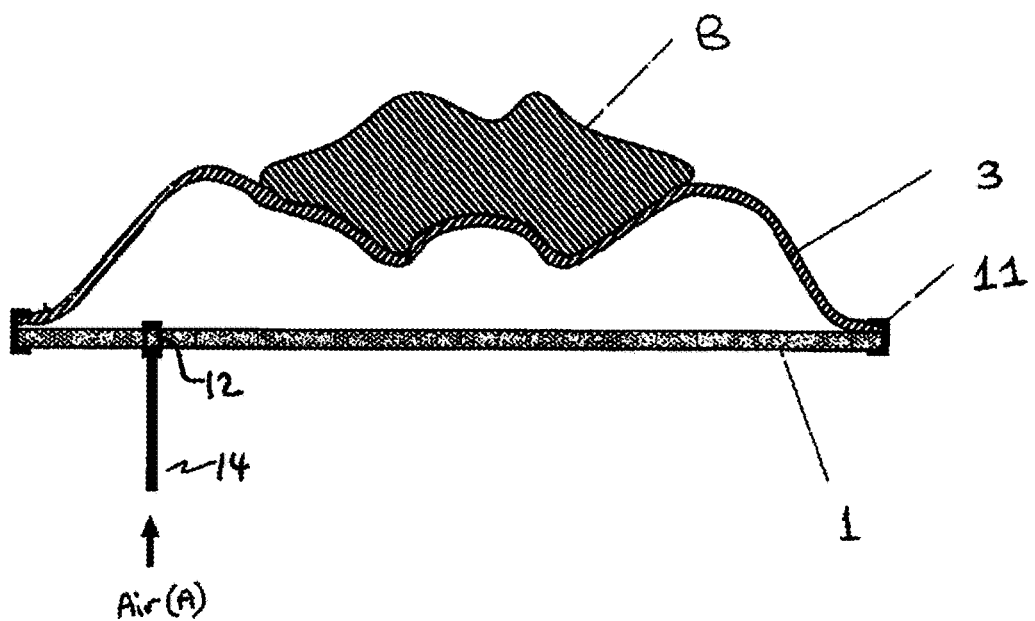
FIG. 4 is a cross-sectional view through the apparatus of the present invention, viewed from above.

Referring now to FIG. 4 of the accompanying drawings, the assembly of the apparatus and system of the present invention will be described further. A rigid platform 1 functioning as a base (referred to herein interchangeably as a "base platform" or "platform") comprises a frame surround 11, which functions as a clamp for connecting the capture sheet 3 to the platform 1, traps the edges of the capture sheet 3, laid on top of the rigid base platform 1.

A bulkhead port 12 in the platform 1 provided with an air inlet pipe 14 shown in FIG. 4 is one example of how air may be delivered between the capture sheet 3 and the rigid base platform 1, in order to drape the capture sheet about the body B by blowing air in through the port 12, thereby urging the flexible, thin, capture sheet 3 towards and about the body B. A suitable pump or blower (not shown) may be situated anywhere, including, in one embodiment, remote from the apparatus and system, and air from the blower may be delivered to the bulkhead port 12 either directly or via tubing 14.

The sheet may be formed of elastic material so as to aid draping, and the sheet may be coated with a sealing material such as polyurethane to aid inflation. This coating is not essential, as air leakage is not a problem provided that the blower for inflating the sheet has sufficient capacity to provide air supply into the space between the sheet and the rigid base platform so as overcome any leakage or seepage through the sheet.

A cross section through a person's body is shown in FIG. 4, applied to the inflated sheet, causing deformation of the sheet. In this way, the shape of the sheet adopts the 3-dimensional form of the person's body.

The person's body may equally well be applied onto the sheet prior to inflation, in which case the shape of the body will impede inflation of the sheet but nevertheless, the same ultimate shape will be achieved on the sheet, and the sheet will once again adopt the shape of the person's body. It is not necessary for the inflation pressure to be so great as to lift the person's body off the base platform, although this is illustrated in FIGS. 5 and 6.

Description of Optical Method for Capturing the 3D Shape

Figure 5:
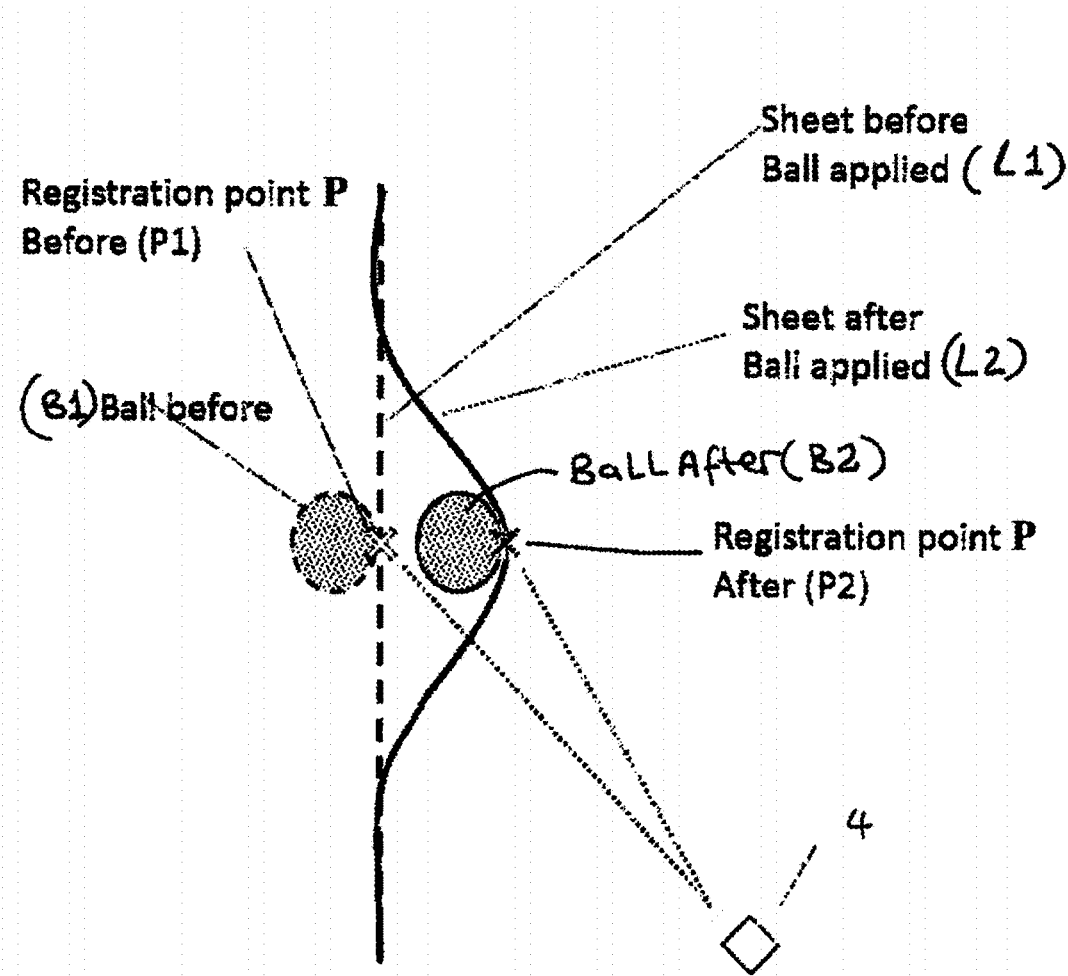
FIG. 5 is a side view of a capture sheet, shown in a vertical orientation; the dotted line illustrates the un-deformed topology of the sheet, prior to application of a body, B. In this case, the body B is represented by a single oval ball, to be pressed into the sheet; the dotted line L1 shows the position of the flexible sheet before application of the body B, and the line L2 shows the position of the flexible sheet after application of the body B; the dotted line B1 shows the position of the body before being in contact with the capture sheet, and the dotted line B2 shows the position of the body B after coming into contact with the capture sheet; the FIG. 6 shows the view from the camera in the assembly shown in FIG. 5.
Figure 6:
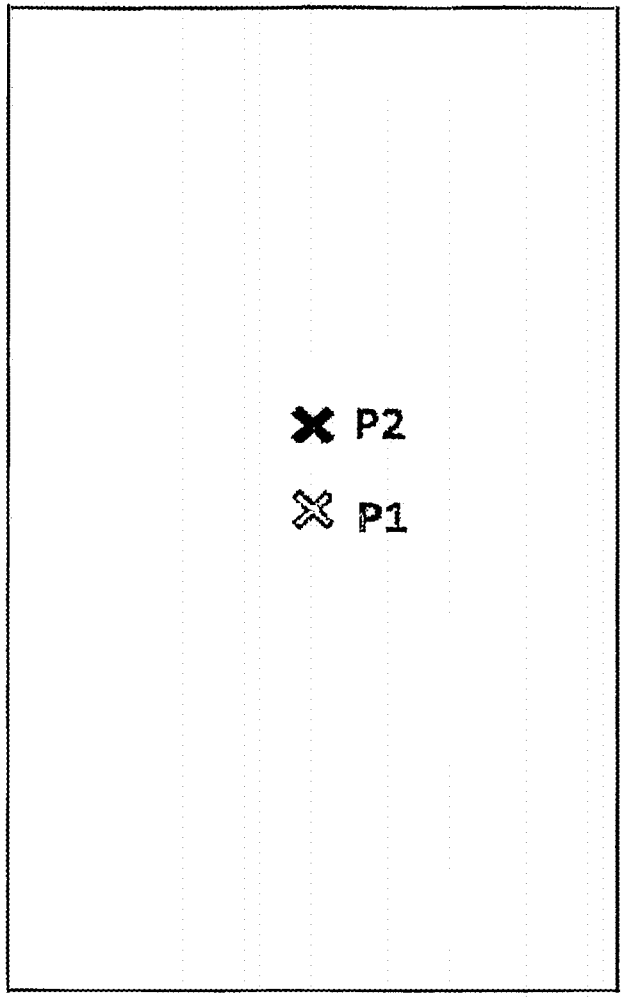

Referring now to FIGS. 5 and 6 in particular, FIG. 5 shows a capture sheet 3 in a vertical orientation, viewed from the side. FIG. 6 shows the view from the camera 4 that is captured when the body B, in this case, a ball, is brought into contact with the capture sheet 3. The ball moves from a body first position (B1) which it occupies just at the point of contact with the capture sheet 3. The dotted line (L1) indicates the initial location of the capture sheet 3, i.e. the un-deformed topology of the capture sheet 3, prior to application of a body (ball) B. In this case, the body, be it an animate (human or animal) body; or an inanimate body) is represented by a single oval ball, to be pressed into the sheet. The line L2 indicates the final location of the capture sheet 3 after the body (ball) has been applied to it and the corresponding position of the body is shown by the ball in position B2.

An initial registration mark, in this case, a registration point, P, is marked on the sheet, in this example, the registration mark is shown as a cross at a single point on the sheet. Prior to application of the ball, this point on the surface of the sheet is at position P1 ("Registration point before"). After application of the ball B, the registration point P moves to position P2 ("Registration point After").

A camera is positioned offset from the direction of motion of point P, which shall be referred to as the z axis, which will be perpendicular to the resting plane of the sheet. In this embodiment, as shown in FIG. 5 the camera is positioned offset below the z axis, at floor level, looking upwards.

FIG. 6 shows the view from the camera. Initially, the camera sees the registration point at position P1. Considering the 3D position of a point as being represented in Cartesian form (x,y,z) with the x value representing the known horizontal position of point P in this view, and the y value representing the known vertical position of point P in this view, z shall represent the deflection of point P in the 3.sup.rd dimension, the z axis. It may be assumed within reasonable limits of accuracy that point P will move predominantly in the z direction, and very little movement in the x direction or y direction.

As the ball is applied to the capture sheet, the capture sheet takes on a new shape, shown by the line L2, and the registration point moves to position P2. This is observed by the camera in FIG. 6 as a movement upwards of the registration point from position P1 to position P2.

Figure 7:
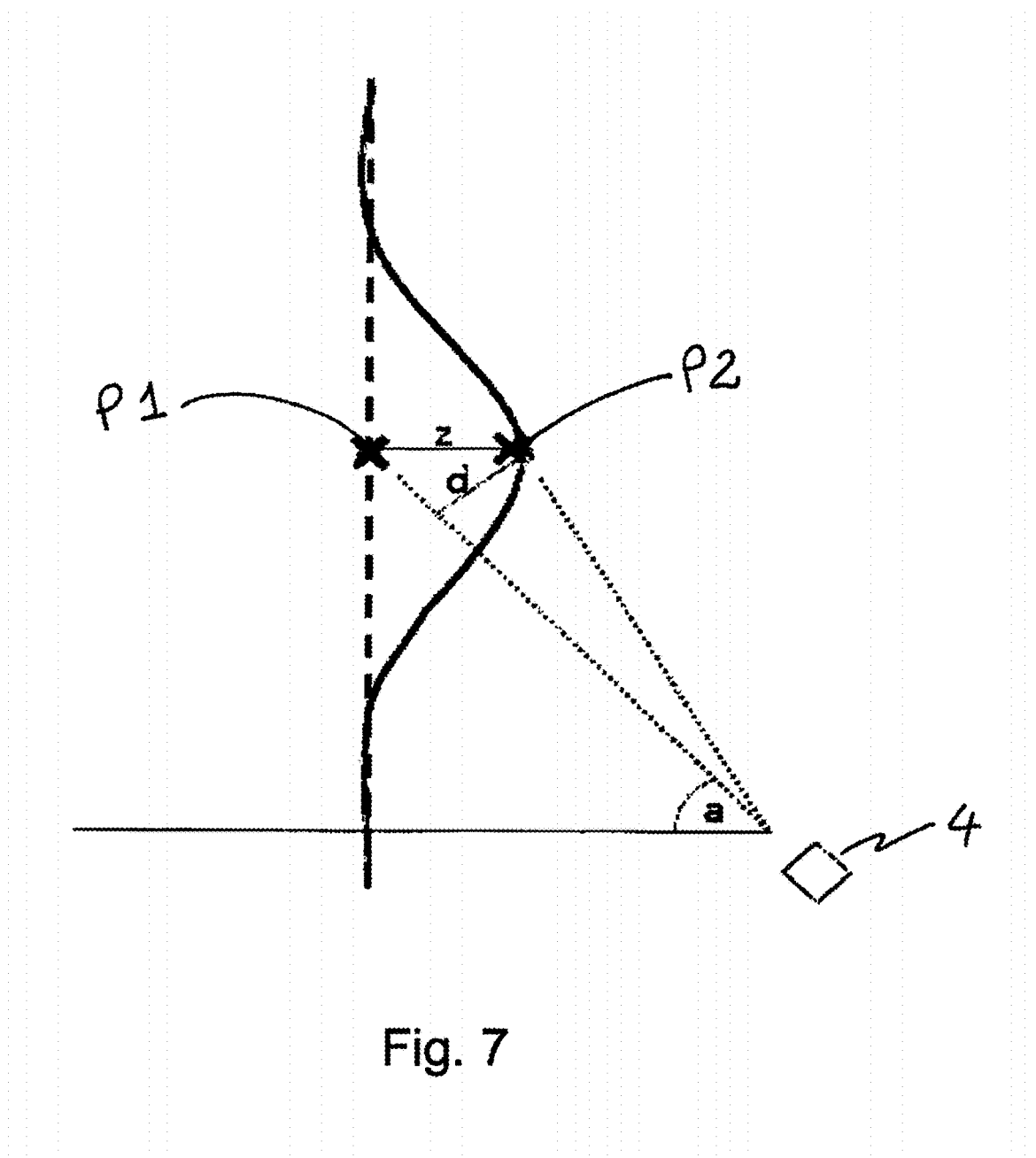
FIG. 7 shows the displacement of the registration mark in the z axis. This is apparent to the camera as a vertical movement of the registration mark by d.
Figure 8:
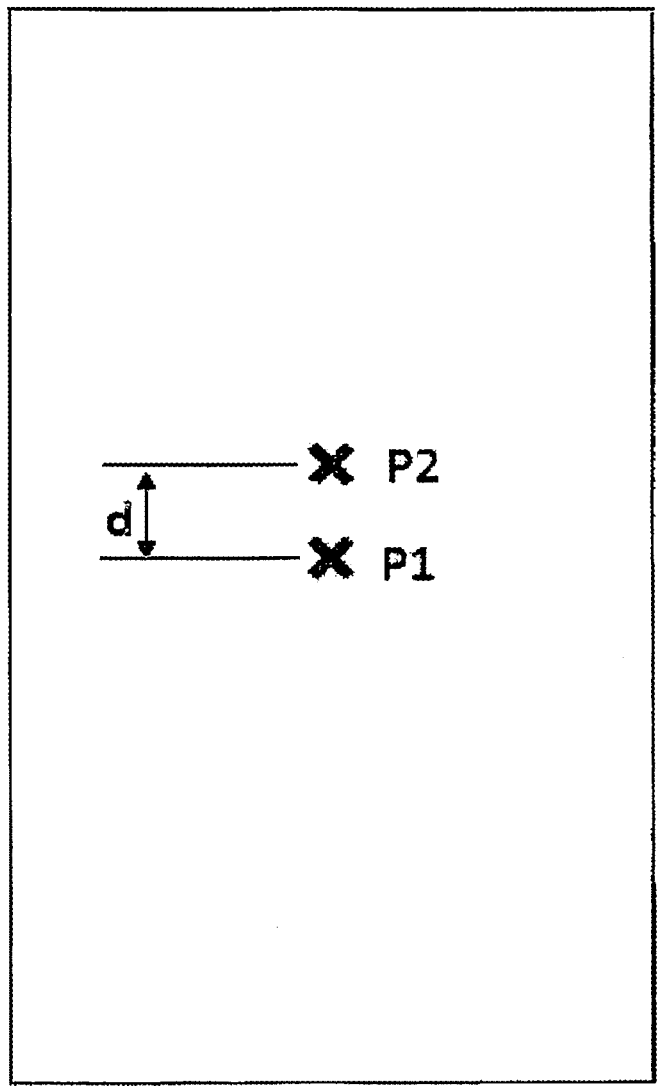
FIG. 8 shows the view from the camera in the assembly shown in FIG. 7; the movement of distance d is shown in the camera view in FIG. 8.

Referring to FIG. 7, the displacement of the registration mark in the z axis is shown as z. This is apparent to the camera as a vertical movement of the registration mark by a distance d. This movement of distance d is shown in the camera view as seen in FIG. 8.

Knowing the position of point P, and the known orientation of the camera, the angle (a) of incidence of the camera is known. Simple trigonometry allows a calculation of z based on d of the form:

$$Z = d / \sin(a)$$

By this means, we now know the z value of the Cartesian coordinates for point P, as well as the x and y already known.

By having a multiple of recognisable registration points in known positions, it is therefore possible to create a 3-dimensional map of the surface of the deflected sheet. Thus, when the sheet drapes to the shape of a body, the body shape can be reconstructed in 3 dimensions.

The registration points on the sheet may take the form of an array of marks in a known geometry, for example as a grid.

For each point, the known y value (vertical position on the sheet) is known, allowing an appropriate viewing angle a to be calculated for the camera view, and thus the appropriate $1/\sin(a)$ scaling factor to derive z.

In one embodiment, the capture sheet could be marked with horizontal lines 30. In this embodiment of the method, it may be assumed that the extremities of the horizontal lines remain undeflected, being trapped by the frame. Therefore, the d value of any point on the line may be determined by its deviation from the straight line between the extremities.

Alternatively, in another embodiment, vertical lines or a grid pattern may be used as the registration marks.

Alternatively, instead of marking the grid or lines directly on the sheet, these may be projected by laser, slide projector, or other means. Provided that the position of the projector is known, simple trigonometry will once again yield the z value of the Cartesian coordinates at any point on the surface.

Numerous software techniques exist for identifying reference points automatically, and calculating their position. Typically, these will take the form of recognising transitions in brightness at the edges of stripes, squares, or other suitable geometries.

Explanation of 'Effective Gravity Reduction'

Figure 9:
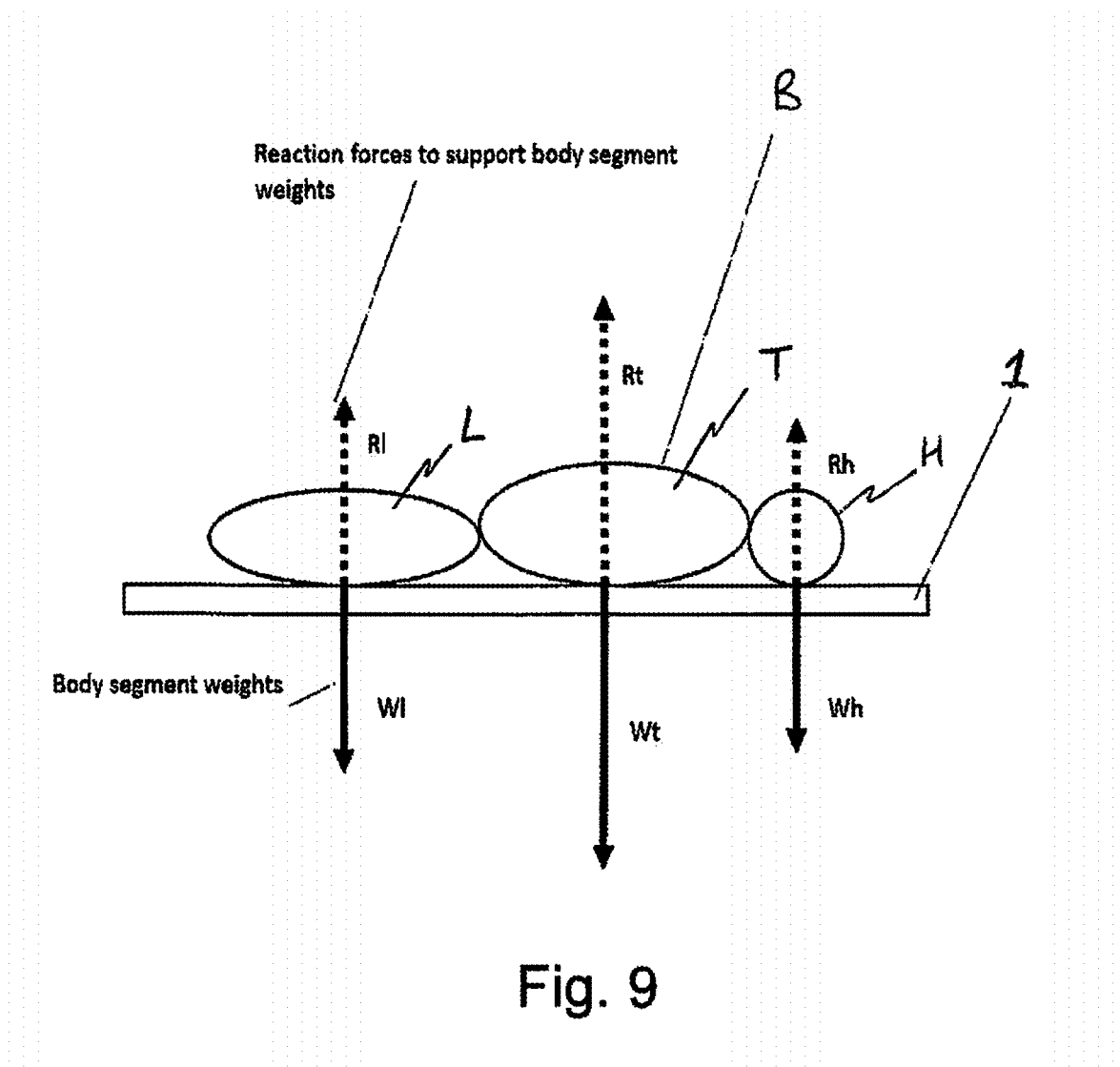
FIG. 9 shows a schematic representation of a body lying on a rigid platform base.

FIG. 9 shows a schematic representation of a body B comprising a nominal body form having a head H, torso T and legs L, is represented lying on a horizontal rigid base platform 1. In FIG. 9, the representation is simplified as a head, torso, and leg section, connected by flexible joints. Each body segment has its respective weight due to gravity, represented in FIG. 9 by the following body segment weights: weight of legs Wl, weight of torso Wt, and weight of head Wh.

On a horizontal platform 1, static equilibrium dictates that the reaction forces associated with the different body parts are equal and opposite to their respective weights. Thus, the reaction forces to support respective body segment weights are Reaction of legs, RL=Wl; Reaction of the torso, Rt=Wt; and Reaction of the head, Rh=Wh. A pressure map of the interface would reveal weights in these proportions associated with each body segment.

Figure 10:
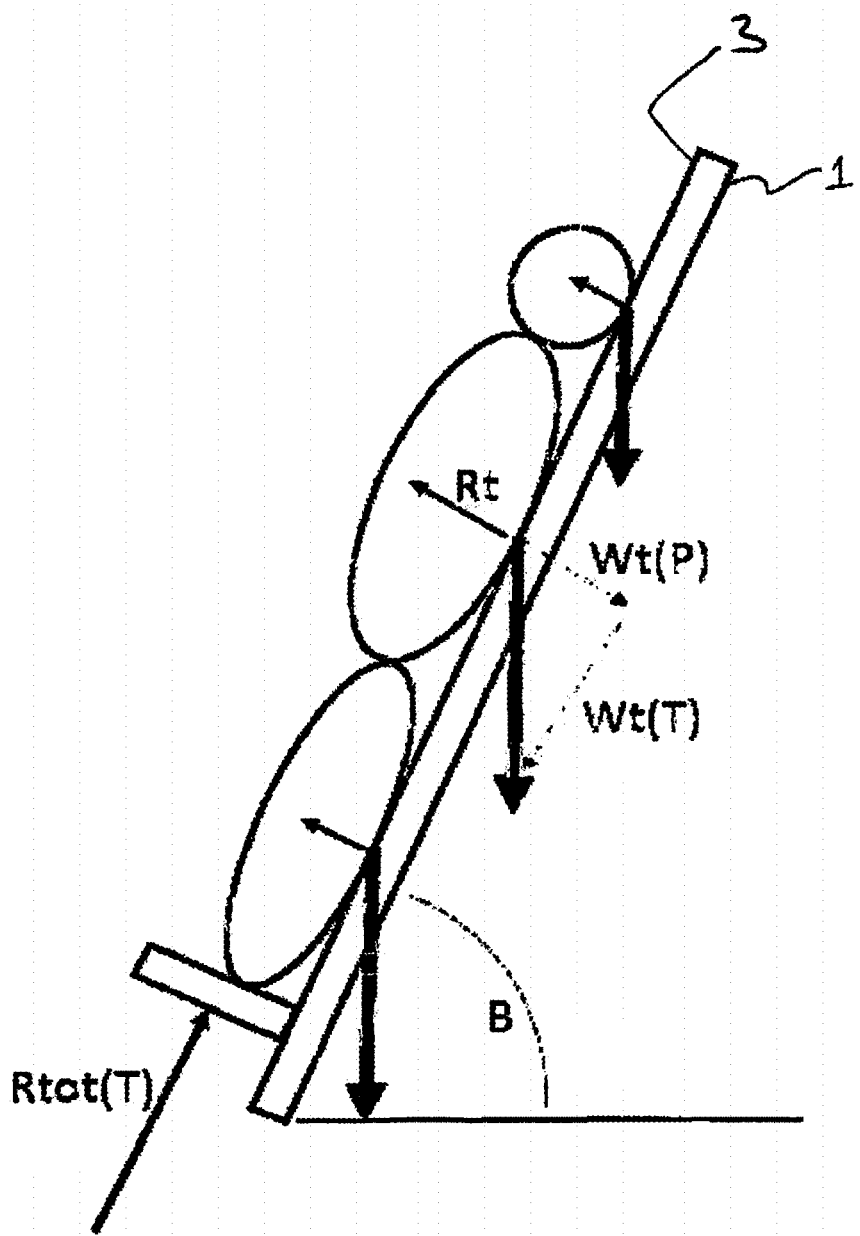
FIG. 10 shows the same schematic body as shown in Figs, this time supported on a rigid board inclined at angle B from the horizontal.

FIG. 10 shows the same schematic body as shown in FIG. 9, now supported on a rigid platform 1 inclined at angle B from the horizontal.

Each body segment, head, torso and legs, still has the same weight due to gravity, respectively Wl, Wt, and Wh. In this embodiment, however, if we assume frictionless contact between the board and the body, reaction from the board can only occur perpendicular to the board. For each body segment, therefore, we can consider weight as consisting of a perpendicular component W(P) perpendicular to the board, and a tangential component W(T) tangential to the board. The reaction force provided by the rigid platform addresses the perpendicular component, whereas the tangential component is entirely provided by a footplate at the lower end of the board, as $R_{tot}(T)$.

For example, considering the torso section: Weight Wt is the sum of components Wt(P) and Wt(T), respectively perpendicular and tangential to the board.

A force sensor at the interface between the torso and the board would therefore record Rt as being equal to Wt(P), whereas Wt(T) would be transferred to the footplate. The new value of Rt can be calculated as Wl.times.cos(B), where B is the inclination of the board from the horizontal.

Importantly, since all body parts are on the same rigid platform inclined at the same angle, they all experience the same reduction in perpendicular reaction force, consisting of a multiplication of the factor cos(B). Therefore, although the reaction forces are reduced, they are still in the same proportions as on the original, horizontal board.

Effectively, the pressure distribution under 'reduced effective gravity' conditions may be observed and measured using the system, apparatus and method of the present invention.

Knowing the angle B, it is therefore possible to measure the distribution of forces or pressures on the inclined rigid platform, and thence calculate the pressure distribution on the body as it would be on a horizontal surface.

This embodiment in which the capture sheet 3 is against an inclined rigid platform 1 is advantageous for the following reasons.

1. It may be inconvenient or uncomfortable in some situations (for example in a shop) to ask somebody to lie down on a flat board. A flat board takes up a lot of floor space, and customers are also sometimes reluctant to do this. The inclined platform uses up less floor space, and can provide the same information.
2. Lying flat under full gravity conditions distorts the skeletal posture and also deforms the soft tissues.

Deriving information (shape, or pressure distribution) from the customer in this way is recording information under less than ideal circumstances. The inclined plane allows a compromise, whereby a realistic recumbent position is adopted, but is not subject to the distorting effects of full gravity.

The optical capture system, apparatus and method of the present invention operates in any of the embodiments described herein, be it with the capture sheet 3 connected to a horizontal rigid platform, for the purposes of direct capture of recumbent position, or from a vertical rigid platform, for a direct capture of standing position, or all points in between, for varying degrees of 'reduced effective gravity' recumbent position.

In an alternative embodiment, a reduced-functionality version of the system, apparatus and method of the present invention is provided which uses a pressure mapping array instead of the flotation fabric. Pressure-mapping involves measuring the interface pressure measurement between a body and a support surface by use of a system of sensors or transducers distributed upon, in or under the surface in the form of a sensor map or otherwise. Typical pressure mapping systems are Xsensor™ or Tekscan™. On its own this reduced functionality embodiment, without the inclusion of a flotation fabric, camera and the capacity to provide 3D image data will provide enhanced or "more accurate" pressure mapping data as the body shape distortion caused when a body interfaces with a support surface at full gravity will be obviated.

This system in this alternative embodiment will give no 3D information about body contours, or spinal curves. However, it will provide a map of the pressure distribution on the base, which may be fitted with a thin standardised cellular foam mattress above the pressure mapping array. Research has demonstrated two important points:

1) Pressure mapping underneath a thin mattress, although not identical to pressure mapping on top of the mattress, is directly related. Interface pressure distribution patterns between customer and mattress can be directly and accurately inferred from pressure patterns between mattress and base. Advantageously, the pressure mapping array is kept flat on a rigid base, making the measurements much less susceptible to artefact, more reproducible, and more accurate, as well as preserving the pressure sensors.
2) Pressure distribution patterns measured at "effective low gravity" using the 10 or 15 degree tilt method, correspond directly to pressure distribution patterns measured at full gravity, requiring only a proprietory scaling and interpretive algorithm.

So, while this alternative, reduced functionality, pressure mapping embodiment of the present invention will not give all the postural information possible with the first embodiment of the system, apparatus and method of the present invention using the capture sheet 3 connected to the rigid platform 1 (i.e the "flotation fabric" approach), the lower functionality, pressure mapping embodiment of the invention enables collection of information which can provide a valid basis for mattress recommendation.

In a still further, alternative embodiment is for the system and apparatus to be enabled with both the pressure mapping and flotation fabric/3D imaging methods so as to capture the biometric data from different perspectives.

In an alternative embodiment, the system may comprise means for adjusting the inflation properties of the air chamber between the flexible sheet/capture sheet and the base platform whereby the inflation properties of the air chamber between the capture sheet and the base platform may be adjusted, for example, by adjusting the inflation pressure, while examining the effects on posture in real time. For example, the 3-dimensional representation of the lumbar, thoracic, and cervical curves can be continuously monitored, while the inflation pressure (and so the firmness) of the support are adjusted. This allows the prescription of the ideal firmness properties of a mattress for the individual. This may be performed with the system horizontal, or inclined with suitable correction factors.

Additional Applications/Uses for the System, Apparatus and Method of the Present Invention It will be understood that, as well as using this method of capturing the shape of the body for categorising the body for optimal mattress selection, the system, apparatus and method of the present invention may be used for other applications.

For example, body shape information captured in accordance with the system, apparatus and method of the present invention may be used in clothing stores to suggest most appropriate sizes and fits of clothing. As another example, the data may be used for ergonomic purposes when customising workplaces, kitchens, or workstations for an individual. Data generated from the system, being available electronically, may be used as a 'body signature' when ordering clothing or furniture online.

Medical applications may include the tracking of the progress of a condition such as oedema, by monitoring the 3-dimensional volume of limbs. Alternatively, for 3-dimensional 'before-and-after' shots associated with reconstructive or cosmetic surgery (e.g. breast reduction).

Sporting applications may include the use of the system at the gym so a user may monitor his progress in modifying physique.

In further embodiments, simplified versions of the system would be capable of measuring the profile of skirtings, covings, and other items used in buildings, to assist in reconstruction, identification, or matching, for instance. Clearly, in this application, references to "body" in this specification are to be construed as referring to an inanimate object.

It will of course, be understood that the present invention is not limited to the details described herein but is defined by the scope of the appended Claims.

The invention claimed is:

1. An apparatus to determine characteristics of a body, the apparatus comprising:
   an inclined platform;
   a flexible capture sheet drapable on the body, the flexible capture sheet, in a rest position, defining a plane having an x-axis, a y-axis, and a z-axis, the flexible capture sheet also having registration marks, wherein the z-axis is perpendicular to the plane, and wherein in the rest position the registration marks are at first positions;
   a blower aimed toward the flexible capture sheet and operable to blow air onto the flexible capture sheet to cause the flexible capture sheet to drape on the body and cause the registration marks to move to second positions; and
   a camera configured to view the registration marks at the second positions of the registration marks obtainable when the flexible capture sheet is draped on the body, wherein a view angle of the camera is offset from the z-axis.

2. The apparatus of claim 1, wherein the camera is a stereoscopic camera configured to stereoscopically photograph the first positions of the registration marks provided on the capture sheet.

3. The apparatus of claim 1, wherein distances between the first positions and the second positions for corresponding registration marks represent the extent of movement of said registration marks when the body deforms said flexible capture sheet, allowing an approximation of a 3-dimensional shape of the body based on said distances.

4. The apparatus of claim 1, further comprising an air chamber defined between the flexible capture sheet and the platform, the air chamber being inflatable.

5. The apparatus of claim 4, wherein the system comprises means for adjusting inflation properties of the air chamber between the flexible sheet and the base platform, while examining inflation effects on the body, in real time.

6. The apparatus of claim 1, wherein the registration marks are provided in a predetermined pattern in a known geometry selected from one or more of the following group: horizontal lines, a grid pattern, and vertical lines.

7. A method of determining characteristics of a shape of a body, the method comprising:
providing an apparatus including an inclined platform, a flexible capture sheet drapable on the body, and a blower aimed toward the flexible capture sheet to cause the flexible capture sheet to drape on the body, the flexible capture sheet, in a rest position, defining a plane having an x-axis, a y-axis and a z-axis, the flexible capture sheet also having registration marks, wherein the z-axis is perpendicular to the plane;
providing a camera configured to view the registration marks at first positions of the registration marks, a view angle of the camera being offset from the z-axis;
recording the first positions with the camera;
applying the body to rest on the flexible capture sheet;
blowing air onto the flexible capture sheet to cause the flexible capture sheet drape on the body and cause the registration marks to move to second positions; and
recording the second positions of the registration marks with the camera.

8. The method of claim 7, further comprising: calculating distances d from the first positions to the second positions along the z-axis based on the recorded first positions and the recorded second positions; correlating the distances d to mattress characteristics of a plurality of mattresses; and selecting a mattress from the plurality of mattresses based on the correlating.

9. The method of claim 8, further comprising recommending the mattress to a person.

10. The method of claim 8, wherein the distances d comprise a first characteristic dataset of the body, the method further comprising: determining a second characteristic dataset of the body at a later time; and comparing the first characteristic dataset and the second characteristic dataset to determine a medical condition of a person comprising the body.

11. The method of claim 10, wherein the registration marks are arranged in a regulated pattern.

12. The method of claim 11, wherein the regulated pattern comprises a plurality of parallel lines.

13. The method of claim 11, further comprising recommending a clothing size based on the correlation.

14. The method of claim 7, further comprising: calculating distances d from the first positions to the second positions along the z-axis based on the recorded first positions and the recorded second positions; and correlating the plurality of distances d to body size characteristics.

* * * * *